United States Patent
Broussard

(10) Patent No.: US 11,660,224 B2
(45) Date of Patent: May 30, 2023

(54) ORTHOPEDIC FIELD SPLINT AND SYSTEM AND METHOD FOR USE OF SAME

(71) Applicant: 3AGJ LLC, Bryan, TX (US)

(72) Inventor: Andrew Broussard, Hemphill, TX (US)

(73) Assignee: 3AGJ LLC, Bryan, TX (US)

( * ) Notice: Subject to any disclaimer, the term of this patent is extended or adjusted under 35 U.S.C. 154(b) by 0 days.

(21) Appl. No.: 16/846,306

(22) Filed: Apr. 11, 2020

(65) Prior Publication Data

US 2021/0128336 A1 May 6, 2021

Related U.S. Application Data

(60) Provisional application No. 62/930,827, filed on Nov. 5, 2019.

(51) Int. Cl.
*A61F 5/00* (2006.01)
*A61F 5/01* (2006.01)
*A61F 5/058* (2006.01)

(52) U.S. Cl.
CPC ............ *A61F 5/013* (2013.01); *A61F 5/0102* (2013.01); *A61F 5/05825* (2013.01)

(58) Field of Classification Search
CPC .... A61F 5/0104; A61F 5/0106; A61F 5/0109; A61F 5/0111; A61F 5/0118; A61F 5/0122; A61F 5/0123; A61F 5/013; A61F 5/0125; A61F 5/026; A61F 5/028; A61F 5/03; A61F 5/058; A61F 5/05816; A61F 5/05825; A61F 5/05841; A61F 5/0585; A61F 5/05858; A61F 5/04

USPC ........................................................ 602/16
See application file for complete search history.

(56) References Cited

U.S. PATENT DOCUMENTS

| | | | |
|---|---|---|---|
| 1,741,011 A | 12/1929 | Carvill | |
| 2,655,916 A | 10/1953 | Timmins | |
| 2,753,864 A | 7/1956 | Weidemann, Jr. | |
| 3,442,270 A | 5/1969 | Steinman | |
| 4,407,276 A | 10/1983 | Bledsoe | |
| 4,941,464 A * | 7/1990 | Scott | A61F 5/04 128/856 |
| 5,170,505 A * | 12/1992 | Rohrer | A41D 11/00 2/126 |
| 5,195,944 A | 3/1993 | Schlogel | |
| 5,514,081 A | 5/1996 | Mann | |
| 5,626,150 A | 5/1997 | Johnson et al. | |
| 5,626,557 A | 5/1997 | Mann | |
| 5,947,916 A | 9/1999 | Riedlinger | |

(Continued)

*Primary Examiner* — Adam Baker
(74) *Attorney, Agent, or Firm* — Scott Griggs; Griggs Bergen LLP

(57) ABSTRACT

An orthopedic field splint and system and method for use of the same are disclosed. In one embodiment of the orthopedic field splint, a body has flexion and extension movement parallel to a longitudinal axis between a horizontal axial plane and a rolled sleeve. A coupling member is hingedly connected to the body in overlapping releasable engagement in a closed retracted position and extending beyond the body in an open extended position. A receiving pocket is connected to the body. The receiving pocket and the coupling member having mutually completing mating forms. Multiple sleeves extend longitudinally through the body and each of the sleeves is parallel to the longitudinal axis and configured to accept a rigid slat.

19 Claims, 10 Drawing Sheets

(56) References Cited

U.S. PATENT DOCUMENTS

| | | | |
|---|---|---|---|
| 5,954,676 | A | 9/1999 | Kramer, III |
| 6,071,257 | A * | 6/2000 | Stojanovic ......... A41D 13/0512 |
| | | | 128/845 |
| 6,106,492 | A | 8/2000 | Darcey |
| 6,719,711 | B1 * | 4/2004 | Islava ................. A61F 5/05816 |
| | | | 128/DIG. 20 |
| 6,871,368 | B2 | 3/2005 | Calkin |
| 7,621,882 | B2 | 11/2009 | Phillips |
| 7,892,253 | B2 | 2/2011 | Exposito et al. |
| 7,959,590 | B2 | 6/2011 | Scott |
| 8,142,378 | B2 | 3/2012 | Reis et al. |
| 8,246,560 | B2 | 8/2012 | Gaylord et al. |
| 8,845,569 | B2 | 9/2014 | Buckman et al. |
| 9,226,841 | B1 * | 1/2016 | Amodt .................. A61F 5/0102 |
| 9,320,639 | B2 | 4/2016 | Serola |
| 9,931,125 | B2 | 4/2018 | Ward et al. |
| 10,016,203 | B2 | 7/2018 | Esposito |
| 2013/0237891 | A1 | 9/2013 | Fryman et al. |
| 2015/0119776 | A1 * | 4/2015 | McNally ............. A61F 5/05841 |
| | | | 602/12 |

* cited by examiner

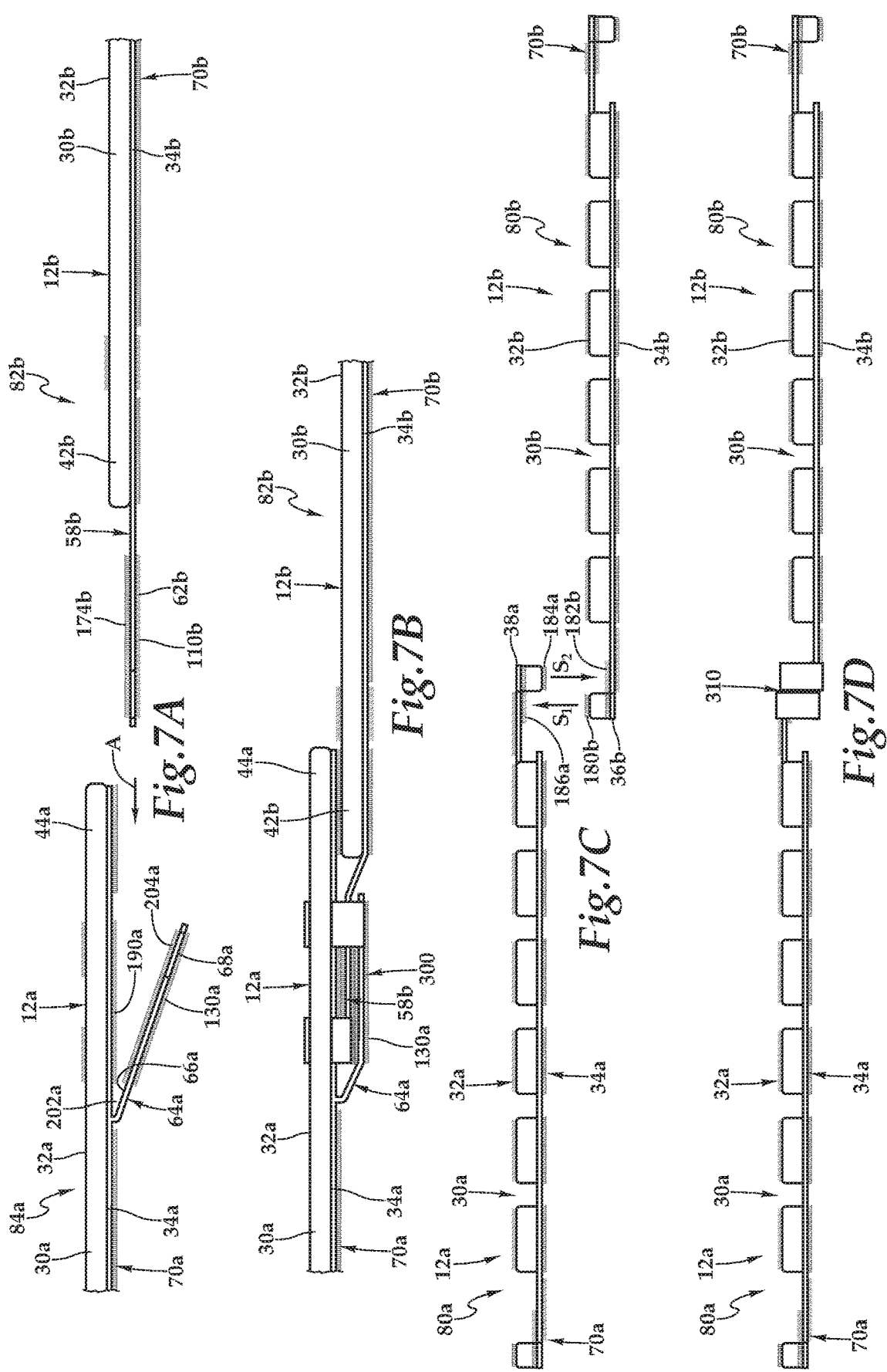

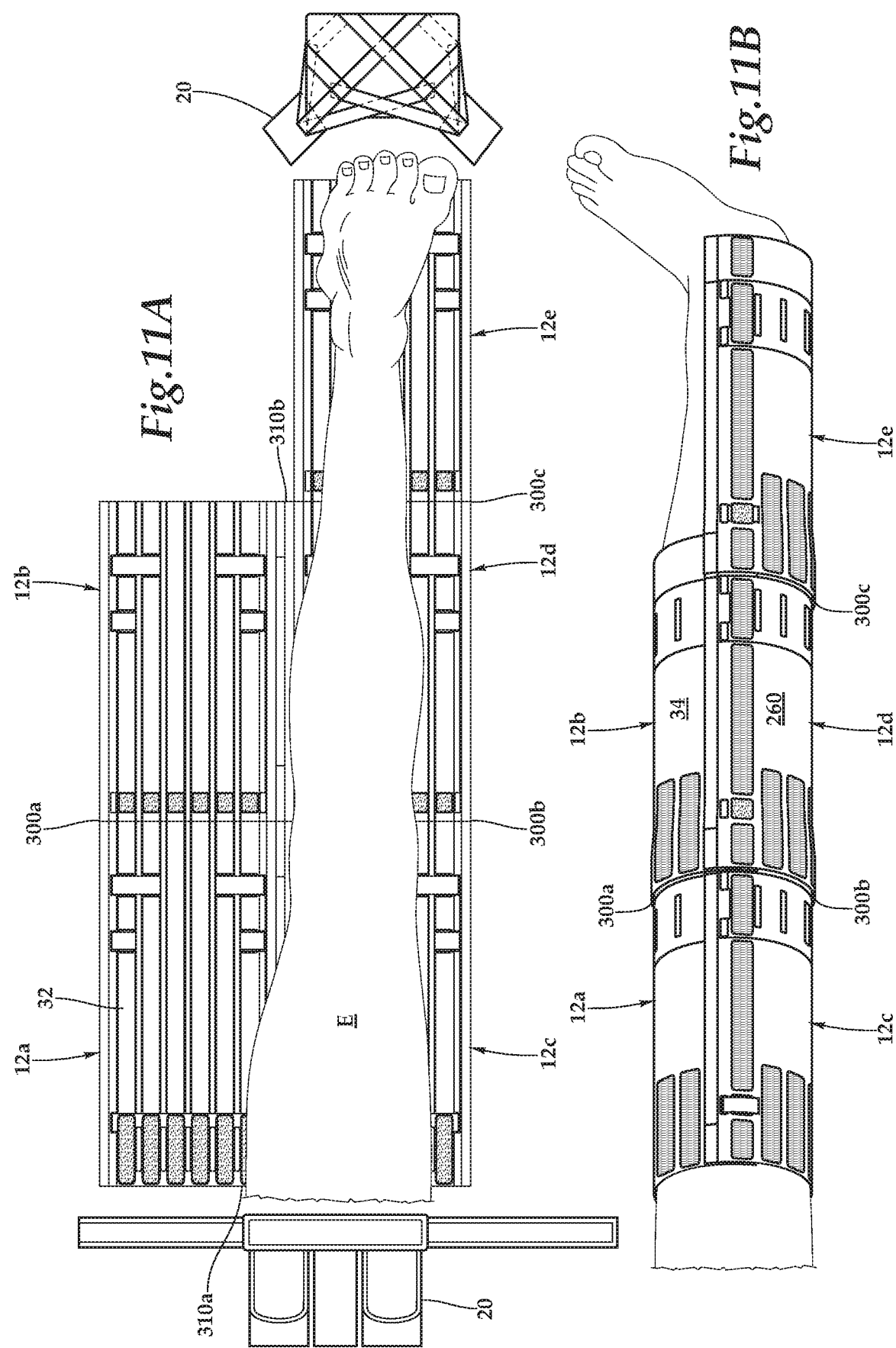

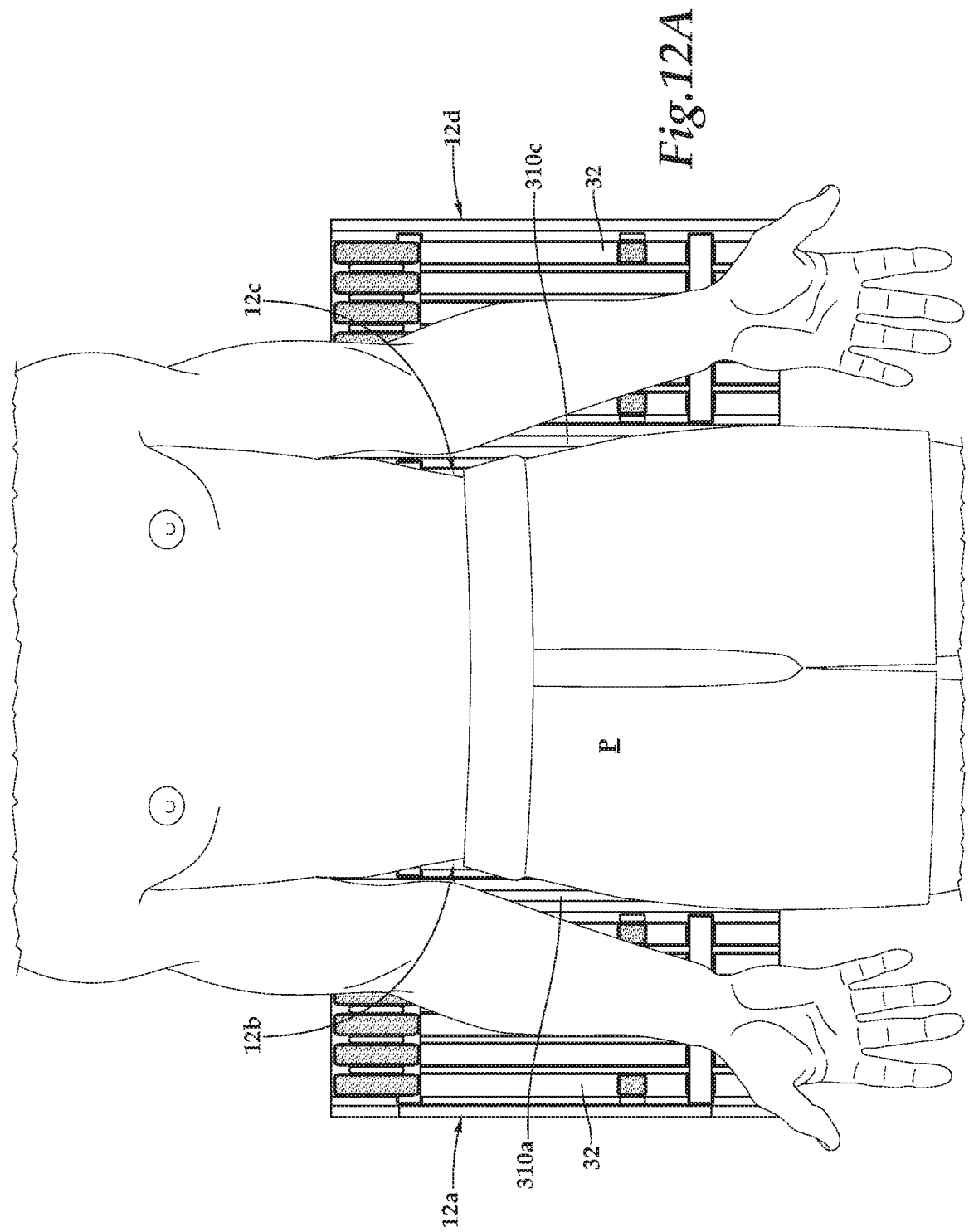

ORTHOPEDIC FIELD SPLINT AND SYSTEM AND METHOD FOR USE OF SAME

PRIORITY STATEMENT & CROSS-REFERENCE TO RELATED APPLICATIONS

This application claims priority from U.S. Patent Application No. 62/930,827, entitled "Orthopedic Field Splint and System and Method for Use of Same" and filed on Nov. 5, 2019, in the name of Andrew Broussard; which is hereby incorporated by reference, in entirety, for all purposes.

TECHNICAL FIELD OF THE INVENTION

This invention relates, in general, to splints utilized in medicine and, in particular, to an orthopedic field splint and system and method for use of the same that immobilizes and protects an injured body part, such as an extremity, and aids in healing and reducing pain.

BACKGROUND OF THE INVENTION

A trauma patient experiencing an injured body part, such as a fracture, for example, presents particular challenges in isolated settings away from medical infrastructure. Often, treating and moving such trauma patients in isolated settings presents difficulties as the trauma patient may be suffering life-threatening injuries and experiencing significant pain. One of the medical goals of field trauma management of a fracture in isolated settings is to minimize movement of the fractured bone, thereby reducing bleeding and providing some comfort. Although there are a number of commercial medical devices and known improvising techniques available for splinting fractures in isolated settings, the existing commercial medical devices and known improvising techniques are not multifunctional, light in weight, or durable. Accordingly, there is a need for improved orthopedic field splint and systems and methods for use of the same that provide improved multifunctionality, weight, and durability.

SUMMARY OF THE INVENTION

It would be advantageous to achieve an orthopedic field splint and systems and methods for use of the same that would improve upon existing limitations in functionality with respect to multifunctionality, weight, and durability. It would also be desirable to enable a mechanical-based medical solution that would provide enhanced functionality as well as improvements in weight and durability. To better address one or more of these concerns, the orthopedic field splint and systems and methods for use of the same are disclosed. In one aspect, one embodiment of the orthopedic field splint includes a body that has flexion and extension movement parallel to a longitudinal axis between a horizontal axial plane and a rolled sleeve. A coupling member is hingedly connected to the body in overlapping releasable engagement in a closed retracted position and extending beyond the body in an open extended position. A receiving pocket is connected to the body. The receiving pocket and the coupling member having mutually completing mating forms. Multiple sleeves extend longitudinally through the body and each of the sleeves is parallel to the longitudinal axis and configured to accept a rigid slat.

In another aspect, one embodiment of a splint system includes multiple instances of the orthopedic field splint, straps, rigid slats, a sling, a traction assembly, and attachment cords. In isolated settings, for example, various combinations of the orthopedic field splints, the straps, the rigid slats, the sling, the traction assembly, and attachment cords may be utilized to splint fractures, including fractures of the radius, ulna, humerus, tibia, fibula, femur, and pelvis. In a further aspect, one embodiment of a method is disclosed that provides a course of action intended to achieve a splint of the fracture in the medical delivery of healthcare. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 7A is a side elevation view depicting the splint system of FIG. 1 having two orthopedic field splints releasably mating end-to-end;

FIG. 7B is a side elevation view depicting the splint system of FIG. 1 having two orthopedic field splints releasably mated end-to-end;

FIG. 7C is an end elevation view depicting the splint system of FIG. 1 having two orthopedic field splints releasably mating side-to-side;

FIG. 7D is an end elevation view depicting the splint system of FIG. 1 having two orthopedic field splints releasably mated side-to-side;

FIG. 11A is a top plan view depicting the splint system of FIG. 1 being utilized to prepare an orthopedic field splint for medical use to address a fractured femur;

FIG. 11B is a perspective view of the splint system of FIGS. 1 and 11A providing the orthopedic field splint for medical use to address the fractured femur;

FIG. 12A is a top plan view depicting the splint system of FIG. 1 being utilized to prepare an orthopedic field splint for medical use to address a fractured pelvis.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
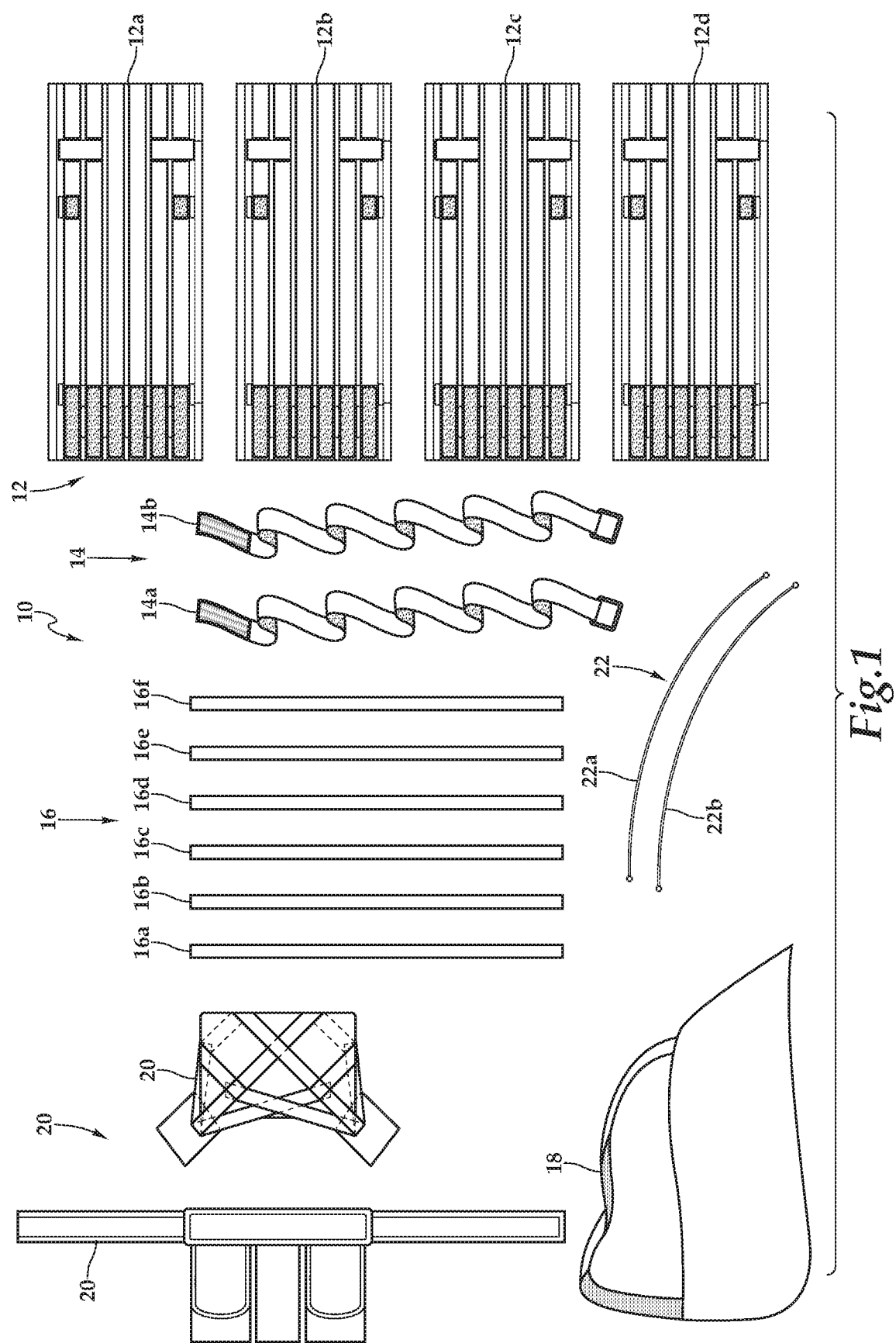
FIG. 1 is a schematic diagram depicting one implementation of a splint system including one embodiment of an orthopedic field splint for treating a fracture according to the teachings presented herein.
Figure 2:
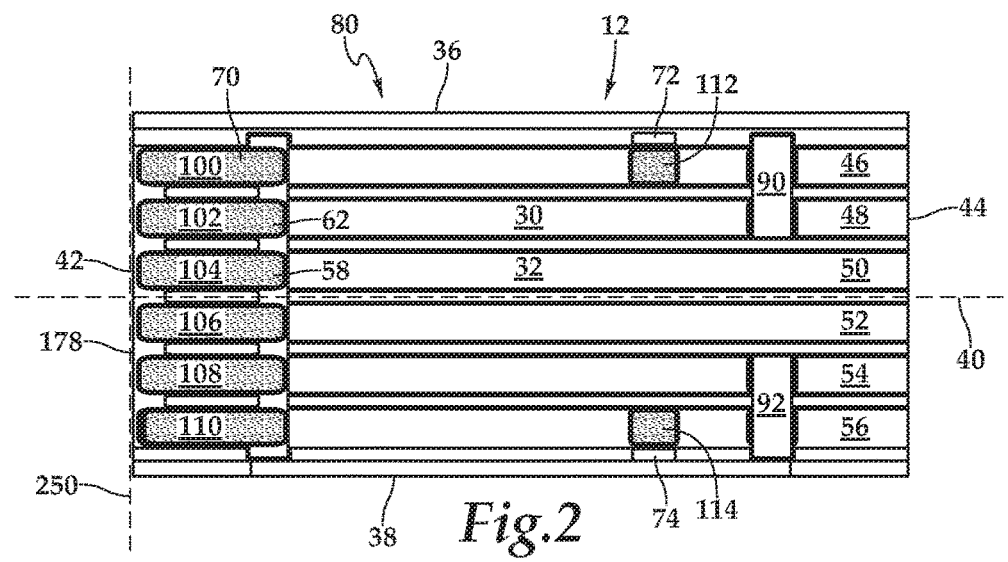
FIG. 2 is a top plan view depicting the orthopedic field splint of FIG. 1 in a collapsed configuration.
Figure 3:
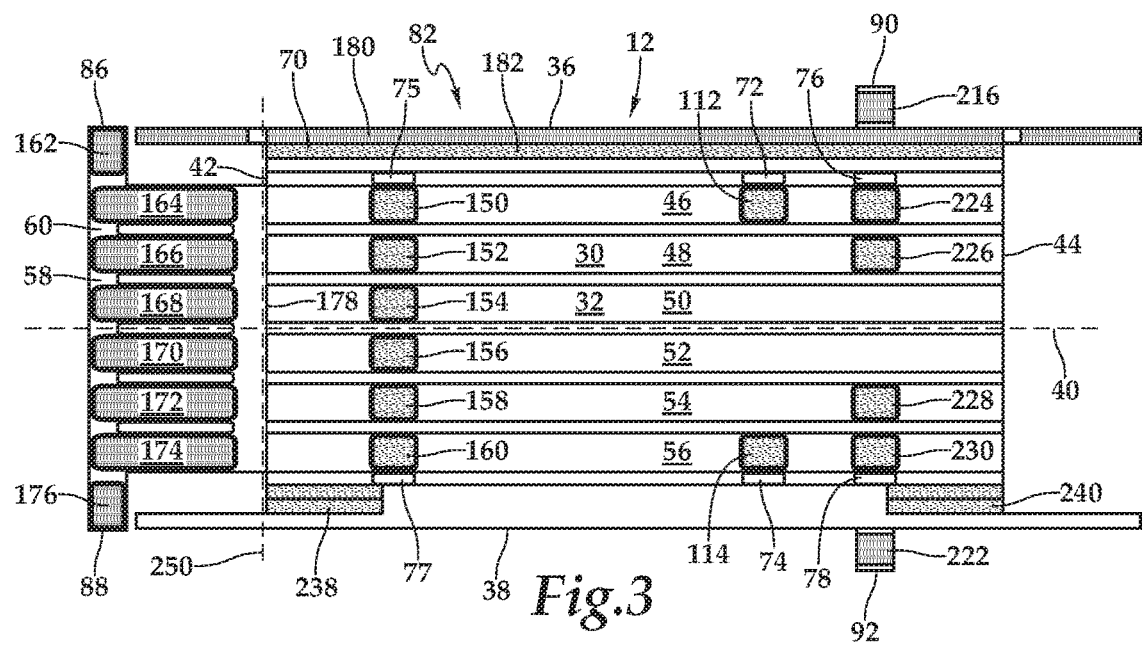
FIG. 3 is a top plan view depicting the orthopedic field splint of FIG. 1 in an open configuration.
Figure 4:
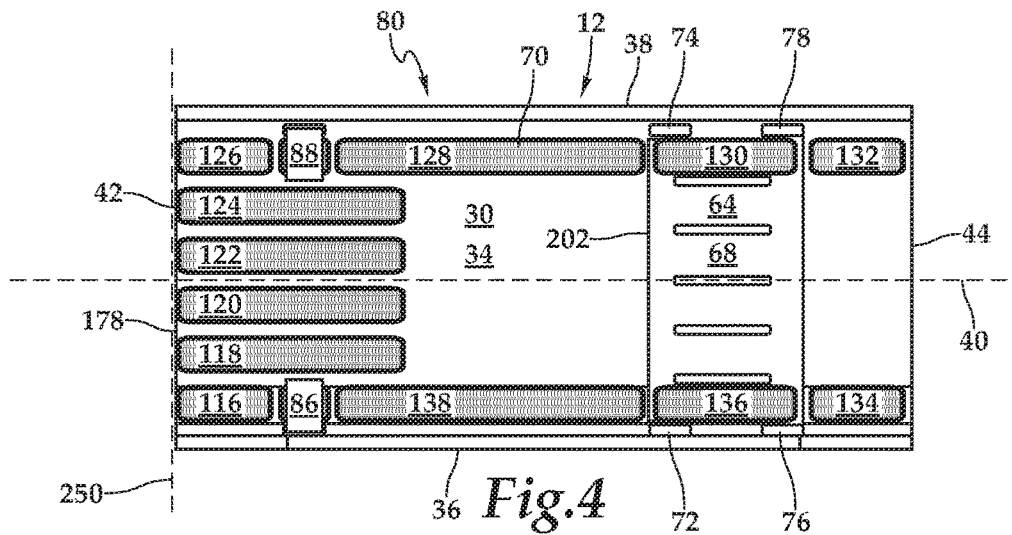
FIG. 4 is a bottom plan view depicting the orthopedic field splint of FIG. 1 in the collapsed configuration.
Figure 5:
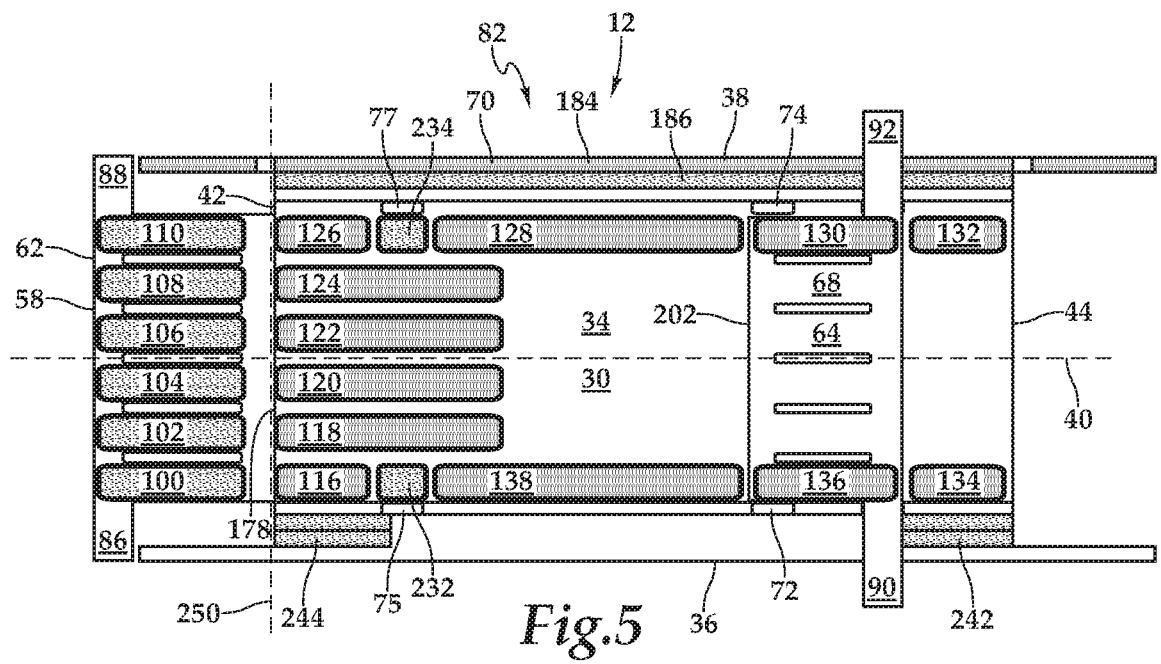
FIG. 5 is a bottom plan view depicting the orthopedic field splint of FIG. 1 in the open configuration.
Figure 6:
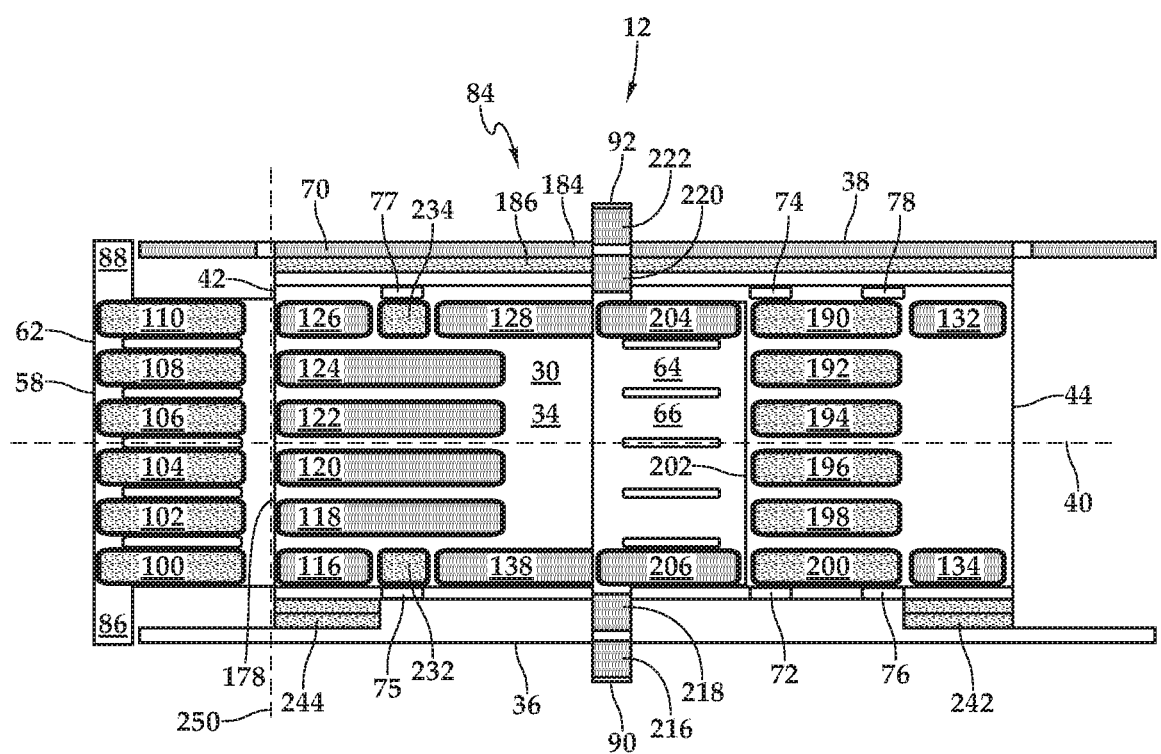
FIG. 6 is a bottom plan view depicting the orthopedic field splint of FIG. 1 in an open expanded configuration.

Referring initially to FIG. 1, therein is depicted one embodiment of a splint system that immobilizes and protects an injured body part, such as an extremity, to aid in healing and reducing pain, which is schematically illustrated and designated 10. The splint system 10 may include one or more orthopedic field splints 12 that are individually designated 12a, 12b, 12c, 12d as well as other components. As shown, straps 14, which are individually designated 14a, 14b, and rigid slats 16, which are individually designated 16a, 16b, 16c, 16d, 16e, 16f, are also depicted. Further, a sling 18, a traction assembly 20, and attachment cords 22, including attachment cord 22a and attachment cord 22b, are included. As will be described in additional detail hereinbelow, the splint system 10 may be deployed as a kit that is multifunctional, light in weight, and durable. In isolated settings, for example, various combinations of orthopedic field splints 12, the straps 14, the rigid slats 16, the sling 18, the traction assembly 20, and attachment cords 22 for positioning, may be utilized to splint fractures, including fractures of the radius, ulna, humerus, tibia, fibula, femur, and pelvis, for example.

Referring now to FIG. 2, FIG. 3, FIG. 4, FIG. 5, and FIG. 6, in one embodiment, the orthopedic field splint 12 includes a body 30 having an inner surface 32 and an outer surface 34. The body 30 also has sides 36, 38 and a longitudinal axis 40 from a connector end 42 to a receptacle end 44. The body 30 may be rectangular in shape. Additionally, the body 30 may include a material selected from KEVLAR materials, GOR-TEX materials, nylon fabrics, ballistic nylon fabrics, polyester and cotton blended fabrics, and polyester fabrics, for example. The inner surface 32 of the body 30 may be configured to contact a body part of a patient.

Sleeves 46, 48, 50, 52, 54, 56 extend longitudinally through the body 30 parallel to the longitudinal axis 40. Each of the sleeves 46, 48, 50, 52, 54, 56 is configured to accept one of the rigid slats 16. A coupling member 58 is connected to the inner surface 32 of the body 30 proximate the connector end 42. The coupling member 58 includes an inside surface 60 and an outside surface 62. The coupling member 58, which has tabs 86, 88, may be rectangular in shape. As shown, the tab 86 is located proximate the side 36 and the tab 88 is located proximate the side 38. Additionally, the coupling member 58 may include a material selected from KEVLAR materials, GOR-TEX materials, nylon fabrics, ballistic nylon fabrics, polyester and cotton blended fabrics, and polyester fabrics, for example.

A receiving pocket 64 is connected to the outer surface 34 of the body 30 proximate to the receptacle end 44. The receiving pocket 64 includes an inside surface 66 and an outside surface 68. The receiving pocket 64, which has tabs 90, 92, may be rectangular in shape. As shown, the tab 90 is located proximate the side 36 and the tab 92 is located proximate the side 38. Additionally, the receiving pocket 64 may include a material selected from KEVLAR materials, GOR-TEX materials, nylon fabrics, ballistic nylon fabrics, polyester and cotton blended fabrics, and polyester fabrics, for example. The coupling member 58 and the receiving pocket 64 may have mutually completing mating forms. Fasteners 70, which may be hook-and-loop fasteners, for example, are located at various places on the body 30. The fasteners 70 may be VELCRO fasteners. A pair of openings 72, 74 is configured to accept one of the straps 14, which is shown as an attachment strap, and configured for movement parallel to the longitudinal axis 40. As shown, the opening 72 is located proximate the side 36 and the opening 74 is located proximate the side 38. Similarly, a pair of openings 76, 78 is configured to accept one of the straps 14, which may be an attachment strap, and is configured for movement parallel to the longitudinal axis 40. The opening 76 may be located proximate the side 36 and the opening 78 may be located proximate the side 38. Additionally, a pair of openings 75, 77 is configured to accept one of the straps 14, which is shown as an attachment strap, and configured for movement parallel to the longitudinal axis 40. As shown, the opening 75 is located proximate the side 36 and the opening 77 is located proximate the side 38. It should be appreciated, however, that the openings 75, 76 are also configured to accept tabs 86, 88 of the coupling member 58; the openings 72, 74, are configured to accept tabs 86, 88 of the coupling member 58 of a separate, but attached orthopedic field splint 12; and the openings 76, 78 are configured to accept tabs 90, 92 of the receiving pocket 64, in an alternate embodiment within the teachings disclosed herein.

As shown, the orthopedic field splint 12 includes a collapsed configuration 80, an open configuration 82, and an open expanded configuration 84. With respect to the collapsed configuration 80, the coupling member 58 is located in overlapping releasable engagement with the inner surface 32 of the body 30 such that the inside surface 60 of the coupling member 58 engages the inner surface 32 of the body 30. The receiving pocket 64 is connected to the outer surface 34 of the body 30 such that the inside surface 66 of the receiving pocket 64 engages the outer surface 34 of the body 30. In the collapsed configuration 80, on one side of the orthopedic field splint 12, the inner surface 32 of the body 30 and the outside surface 62 of the coupling member 58 are present. On the other side of the orthopedic field splint 12, the outer surface 34 of the body 30 and the outside surface 68 of the receiving pocket 64 are present.

With respect to the open configuration 82, the coupling member 58 is released from the inner surface 32 of the body 30 and extends beyond the connector end 42 of the body 30 such that the inside surface 60 of the coupling member 58 is adjacent the inner surface 32 of the body 30. Additionally, the outside surface 62 of the coupling member 58 is adjacent the outer surface 34 of the body 30. Similar to the collapsed configuration 80, in the open configuration 82, the receiving pocket 64 is connected to the outer surface 34 of the body 30 such that the inside surface 66 of the receiving pocket 64 engages the outer surface 34 of the body 30. In the open configuration 82, on one side of the orthopedic field splint 12, the inner surface 32 of the body 30 and the inside surface 60 of the coupling member 58 are present. On the other side of the orthopedic field splint 12, in the open configuration 82, the outer surface 34 of the body 30 and the outside surface 68 of the receiving pocket 64 are present.

With respect to the open expanded configuration 84, the coupling member 58 is released from the inner surface 32 of the body 30 and extends beyond the connector end 42 of the body 30 such that the inside surface 60 of the coupling member 58 is adjacent the inner surface 32 of the body 30. Additionally, the outside surface 62 of the coupling member 58 is adjacent the outside surface 34 of the body 30. The receiving pocket 64 is connected to the outer surface 32 of the body 30 and unfolded such that the outside surface 68 of the receiving pocket 64 engages the outer surface 34 of the body 30 and the inside surface 66 of the receiving pocket 64 is exposed. In the open expanded configuration 84, on one side of the orthopedic field splint 12, the inner surface 32 of the body 30, the inside surface 60 of the coupling member 58 is present. On the other side of the orthopedic field splint 12, the outer surface 34 of the body 30, and the outside surface 62 of the coupling member 58, and the inside surface 66 of the receiving pocket 64 present.

With respect to the fasteners 70, as mentioned, the fasteners 70 may include hook-and-loop fasteners. It should be appreciated that the fasteners 70 may include snaps, buttons, metal hooks, hook-and-loop fasteners, or a combination thereof. As shown, with respect to the collapsed configuration 80, on the inner surface 32, loop fasteners 100, 102, 104, 106, 108, 110 are located on the outside surface 62 of the coupling member 58. Additionally, a loop fastener 112 is located near the opening 72 and a loop fastener 114 is located near the opening 74. The outer surface 34 includes hook fasteners 116, 118, 120, 122, 124, 126 proximate the connector end 42. Hook fasteners 128, 130, 132 are located along the side 38 of the outer surface 34 and hook fasteners 134, 136, 138 are located along the side 36 of the outer surface 34.

In the open configuration 82, with the coupling member 58 extending beyond the connector end 42 of the body 30, the inner surface 32 includes loop fasteners 150, 152, 154, 156, 158, 160 proximate the connector end 42, which are exposed in the open configuration 82. Hook fasteners 162, 164, 166, 168, 170, 172, 174, 176 are on the inside surface 60 of the coupling member 58 and are exposed in the open configuration 82. Loop fasteners 224, 226, 228, and 230 on the inner surface 34 of the body 30 are exposed when the tabs 90, 92 are detached in the open configuration. Loop fasteners 232, 234 on the outer surface 34 of the body 30 are exposed when the tabs 86, 88 are detached in the open configuration 82. In the open configuration 82, the sides 36, 38 are unfurled exposing a loop fastener 238, located on the inner surface 32 of the orthopedic field splint 12 proximate the connector end 42 and the side 38; a loop fastener 240, located on the inner surface 32 of the orthopedic field splint 12 proximate the receptacle end 44 and the side 38; a loop fastener 242, located on the outer surface 34 of the orthopedic field splint 12 proximate the receptacle end 44 and the side 36; and a loop fastener 244, located on the outer surface 34 of the orthopedic field splint 12 proximate the connector end 42 and the side 36. In the collapsed configuration 80, on the other hand, the loop fasteners 150, 152, 154, 156, 158, 160 are respectively joined to the hook fasteners 164, 166, 168, 170, 172, 174. That is, as shown, a hinge 178 connects the coupling member 58 to the outer surface 34 such that the coupling member 58 releasably engages the inner surface 32. It should be appreciated, however, that the coupling member 58 may be hingedly connected to the inner surface 32 in an alternate embodiment within the teachings disclosed herein. The loop fasteners 150, 152, 154, 156, 158, 160 join with the hook fasteners 164, 166, 168, 170, 172, 174 to establish the overlapping releasable engagement of the coupling member 58 to the inner surface 32 of the body 30.

In the collapsed configuration 80, a hook fastener 180 and a loop fastener 182 on the outer surface 34 at the side 36 have a furled configuration and are not visible. In the open configuration 82, the hook fastener 180 and the loop fastener 182 on the inner surface 32 have an unfurled configuration and are visible. Similarly, in the collapsed configuration 80, a hook fastener 184 and a loop fastener 186 on the outer surface 34 of the body 30 at the side 38 have a furled configuration and are not visible. In the open configuration 82, the hook fastener 184 and the loop fastener 186 on the outer surface 34 have an unfurled configuration and are visible. In the open expanded configuration 84, the receiving pocket 64 is exposed to show loop fasteners 190, 192, 194, 196, 198, 200 secured to the outer surface 34 proximate a hinge 202 of the receiving pocket 64. The loop fasteners 190, 192, 194, 196, 198, 200 join hook fasteners 204, 206 positioned on the inside surface 66 of the receiving pocket 64. Additionally, hook fasteners 216, 218, 220, 222 are positioned on the inside surface 66 of the tabs 90, 92 of the receiving pocket 64. As mentioned, the inner surface 32 of the body 30 may be configured to contact a body part of a patient. Accordingly, in some embodiments, the fasteners 70 on the inner surface 32 are loop fasteners and the fasteners 70 on the outer surface 34 are hook fasteners.

Figure 8A:
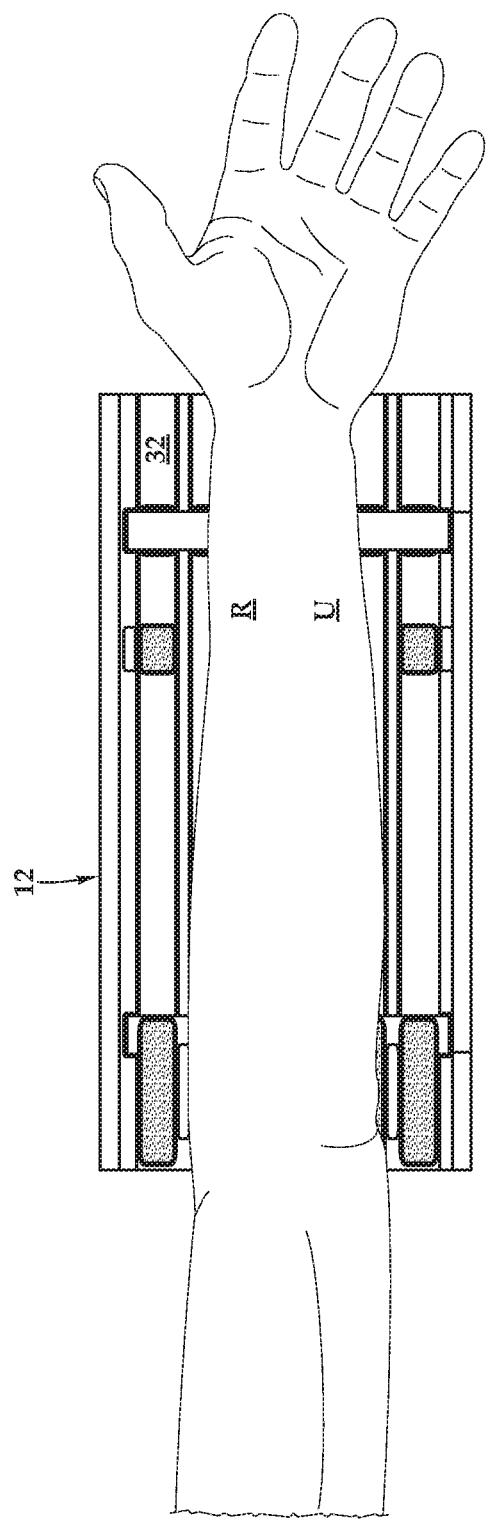
FIG. 8A is a top plan view depicting the splint system of FIG. 1 being utilized to prepare an orthopedic field splint for medical use to address a fractured radius, for example.
Figure 8B:
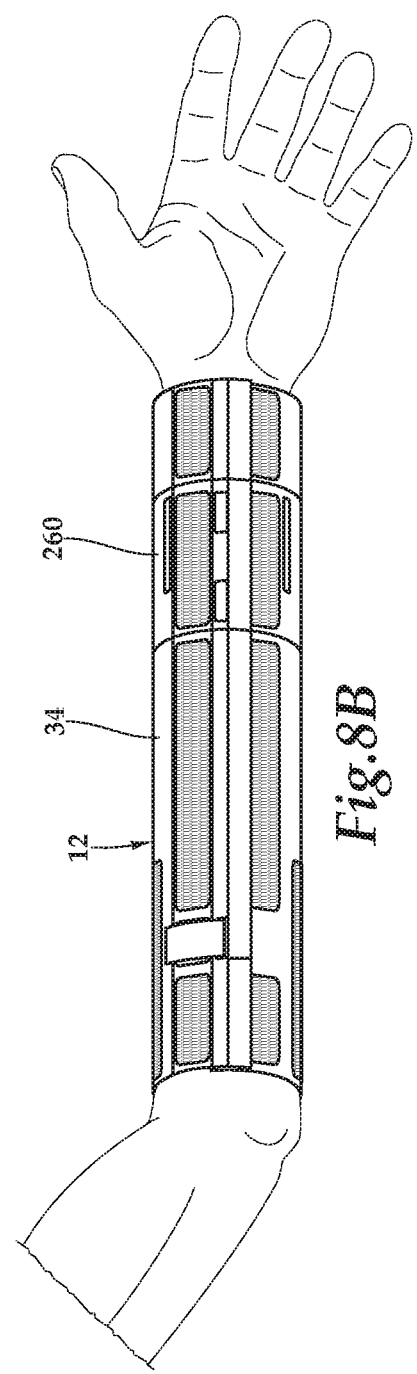
FIG. 8B is a perspective view of the splint system of FIGS. 1 and 8A providing the orthopedic field splint for medical use to address the fractured radius.

In operation, to prepare a splint, the body 30 of the orthopedic field splint 12 has flexion movement parallel to the longitudinal axis 40 from a horizontal axial plane 250 to a rolled sleeve 260 (see FIG. 8B). The body 30 has extension movement parallel to the longitudinal axis 40 from the rolled sleeve 260 to the horizontal axial plane 260 (see FIG. 8B). As mentioned, the splint system 10 includes multiple instances of the orthopedic field splint 12, the straps 14, the rigid slats 16, the sling 18, and the traction assembly 20. In isolated settings, for example, various combinations of the orthopedic field splints 12, the straps 14, the rigid slats 16, the sling 18, and the traction assembly 20 may be utilized to splint fractures, including fractures of the radius (FIGS. 8A, 8B), ulna (FIGS. 8A, 8B), humerus (FIGS. 9A, 9B), tibia (FIGS. 10A, 10B), fibula (FIGS. 10A, 10B), femur (FIGS. 11A, 11B), and pelvis (FIGS. 12A, 12B), for example. To prepare the necessary splint, in many instances, such as the humerus (FIGS. 9A, 9B), tibia (FIGS. 10A, 10B), fibula (FIGS. 10A, 10B), femur (FIGS. 11A, 11B), and pelvis (FIGS. 12A, 12B), it is necessary to mate two or more orthopedic field splints 12 end-to-end (FIGS. 7A, 7B) or side-to-side (FIGS. 7C, 7D), or a combination thereof.

The splint system 10 provides a compact, collapsible, and lightweight organized medical scheme that is portable while being useful in isolated settings. As will be discussed in further detail hereinbelow, the splint system 10 may be expediently configured and provide a single-use platform for multiple fractures, including fractures of the radius (FIGS. 8A, 8B), ulna (FIGS. 8A, 8B), humerus (FIGS. 9A, 9B), tibia (FIGS. 10A, 10B), fibula (FIGS. 10A, 10B), femur (FIGS. 11A, 11B), and pelvis (FIGS. 12A, 12B), for example.

With reference to FIGS. 7A and 7B, two orthopedic field splints 12a and 12b may be connected end-to-end with a connection 300. The orthopedic field splint 12a is positioned in the open expanded configuration 84a, where the body 30a includes the inner surface 32a and the outer surface 34a as well as fasteners 70a. At the receptacle end 44a, the receiving pocket 64a is opened with the loop fastener 190a secured to the outer surface 34a proximate the hinge 202a. The hook fastener 204a is positioned on the inside surface 66a of the receiving pocket 64a. The hook fastener 130a is positioned on the outside surface 68a of the receiving pocket 64a.

The orthopedic field splint 12b is positioned in the open configuration 82b, where the body 30b includes the inner surface 32b and the outer surface 34b as well as fastener 70b. At the connector end 42b, the coupling member 58b is extended with the hook fastener 174b positioned on inside surface 60b and the loop fastener 110b positioned on the outside surface 62b. As shown by arrow A, the receiving pocket 64a and the coupling member 58b having mutually completing mating forms. The coupling member 58b is releasably engaged with the receiving pocket 64a and held therein by the hook-and-loop fastener bonds of the fasteners 70a, 70b to form the connection 300.

With reference to FIGS. 7C and 7D, two orthopedic field splints 12a and 12b may be connected side-to-side with a connection 310. The orthopedic field splint 12a is positioned in the collapsed configuration 80a, where the body 30a includes the inner surface 32a and the outer surface 34a as well as fasteners 70a. The hook fastener 184a and the loop fastener 186a on the outer surface 34a at the side 38a have the unfurled configuration. Similarly, the orthopedic field splint 12b is positioned in the collapsed configuration 80b, where the body 30b includes the inner surface 32b and the outer surface 34b as well as fasteners 70b. The hook fastener 180b and the loop fastener 182b on the inner surface 32a at the side 36b have the unfurled configuration. As shown by arrows S₁ and S₂, the side 38a is releasably engaged with the side 36b and held therein by the hook-and-loop fastener bonds of the fasteners 70a, 70b to form the connection 310.

Figure 9A:
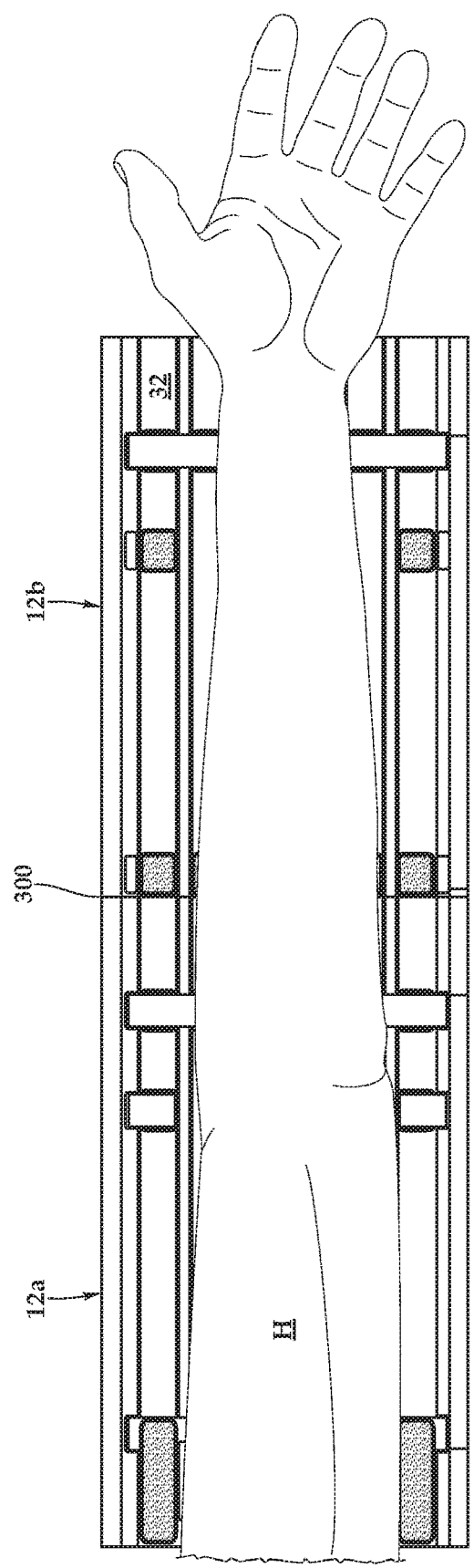
FIG. 9A is a top plan view depicting the splint system of FIG. 1 being utilized to prepare an orthopedic field splint for medical use to address a fractured humerus, for example.
Figure 9B:
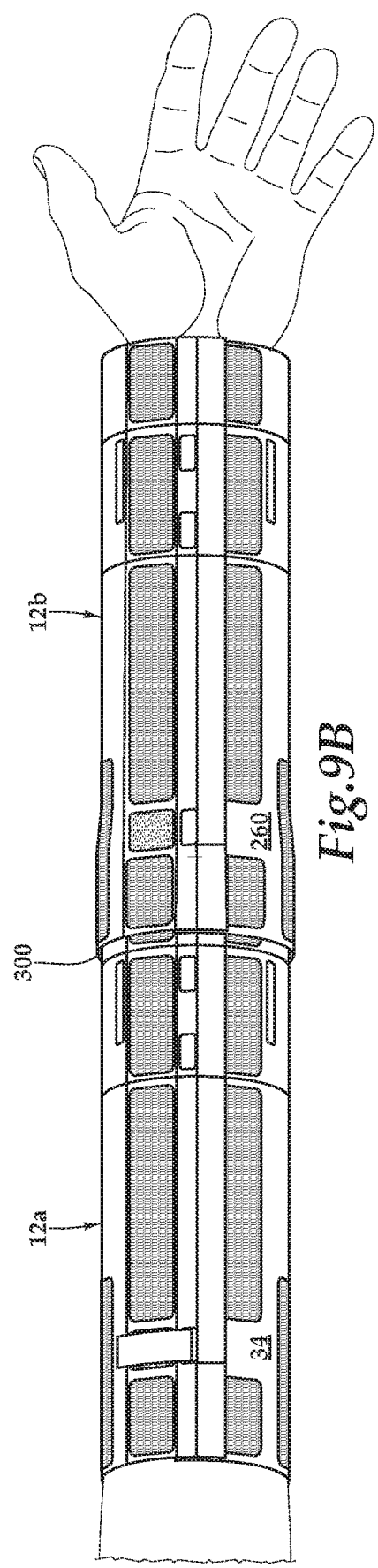
FIG. 9B is a perspective view of the splint system of FIGS. 1 and 9A providing the orthopedic field splint for medical use to address the fractured humerus.
Figure 10A:
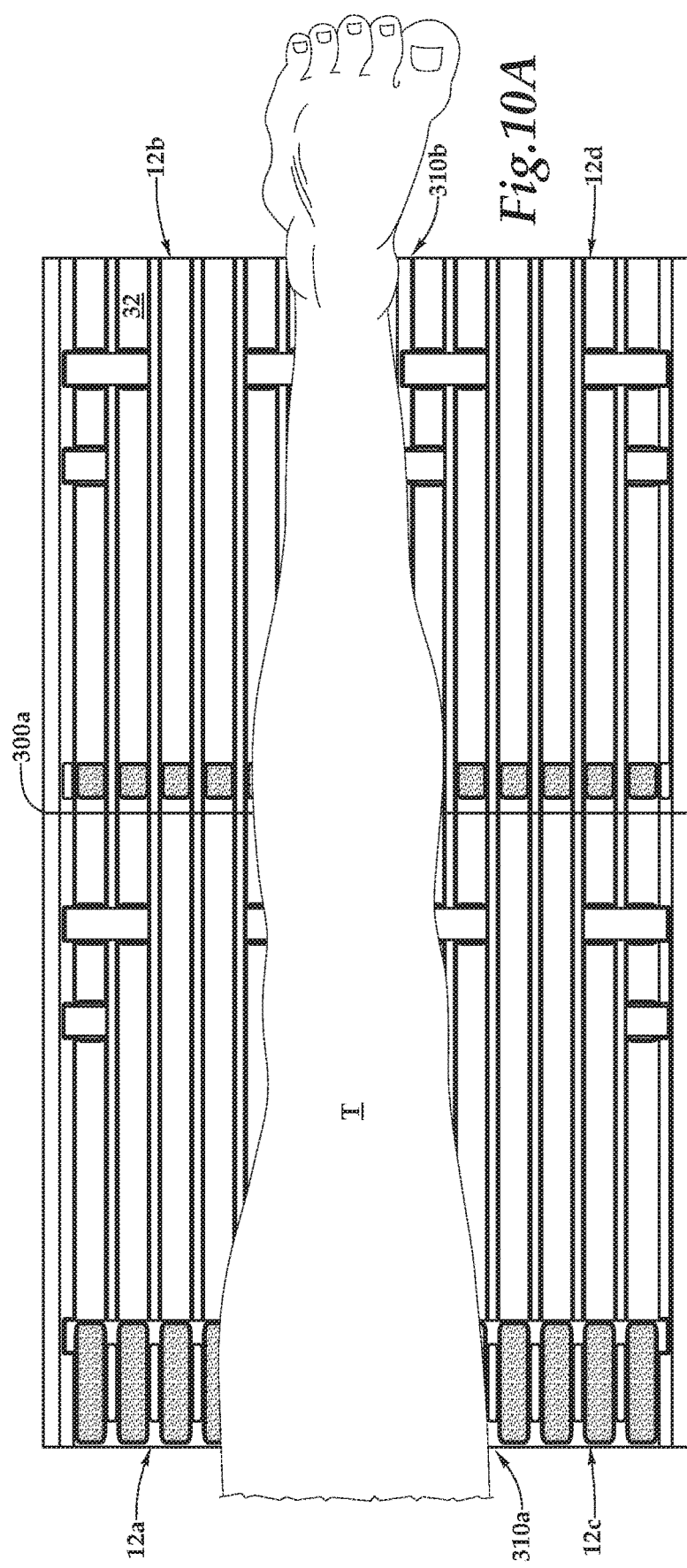
FIG. 10A is a top plan view depicting the splint system of FIG. 1 being utilized to prepare an orthopedic field splint for medical use to address a fractured tibia, for example.
Figure 10B:
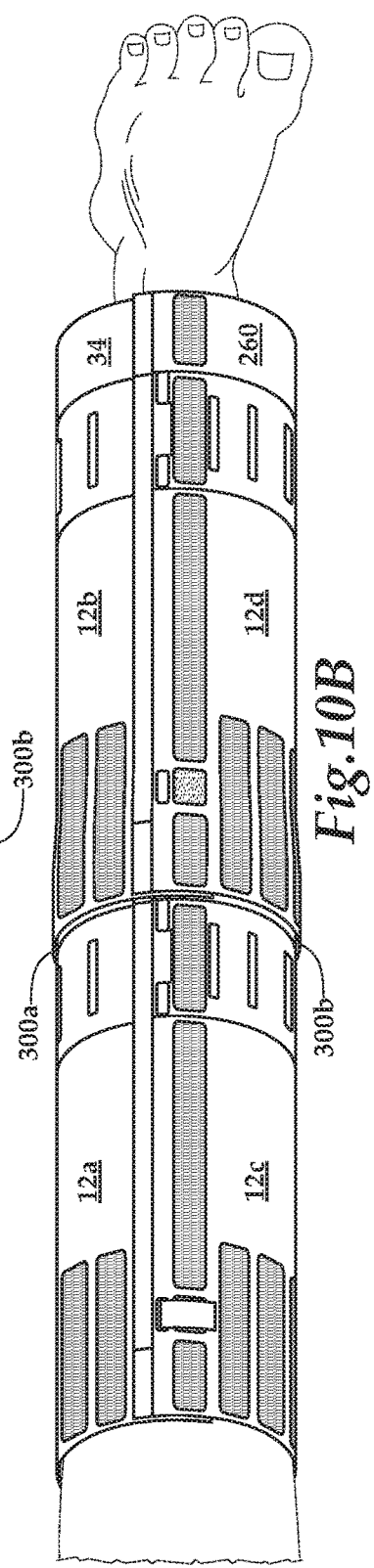
FIG. 10B is a perspective view of the splint system of FIGS. 1 and 10A providing the orthopedic field splint for medical use to address the fractured tibia.

As alluded, using the connection 300 and the connection 310, as appropriate, fractures of the radius (FIGS. 8A, 8B), ulna (FIGS. 8A, 8B), humerus (FIGS. 9A, 9B), tibia (FIGS. 10A, 10B), fibula (FIGS. 10A, 10B), femur (FIGS. 11A, 11B), and pelvis (FIGS. 12A, 12B), for example, may be medically addressed. More particularly, in FIG. 8A and FIG. 8B, the splint system 10 utilizes the orthopedic field splint 12 to splint a radius R or an ulna U. In FIG. 9A and FIG. 9B, the splint system 10 utilizes the orthopedic field splint 12a and the orthopedic field splint 12b with an end-to-end connection 300 to splint a humerus H. In FIG. 10A and FIG. 10B, the splint system 10 utilizes the orthopedic field splint 12a, the orthopedic field splint 12b, the orthopedic field splint 12c, and the orthopedic field splint 12d with end-to-end connections 300a, 300b and side-to-side connections 310a, 310b to splint a fibula F or tibia T.

Figure 12B:
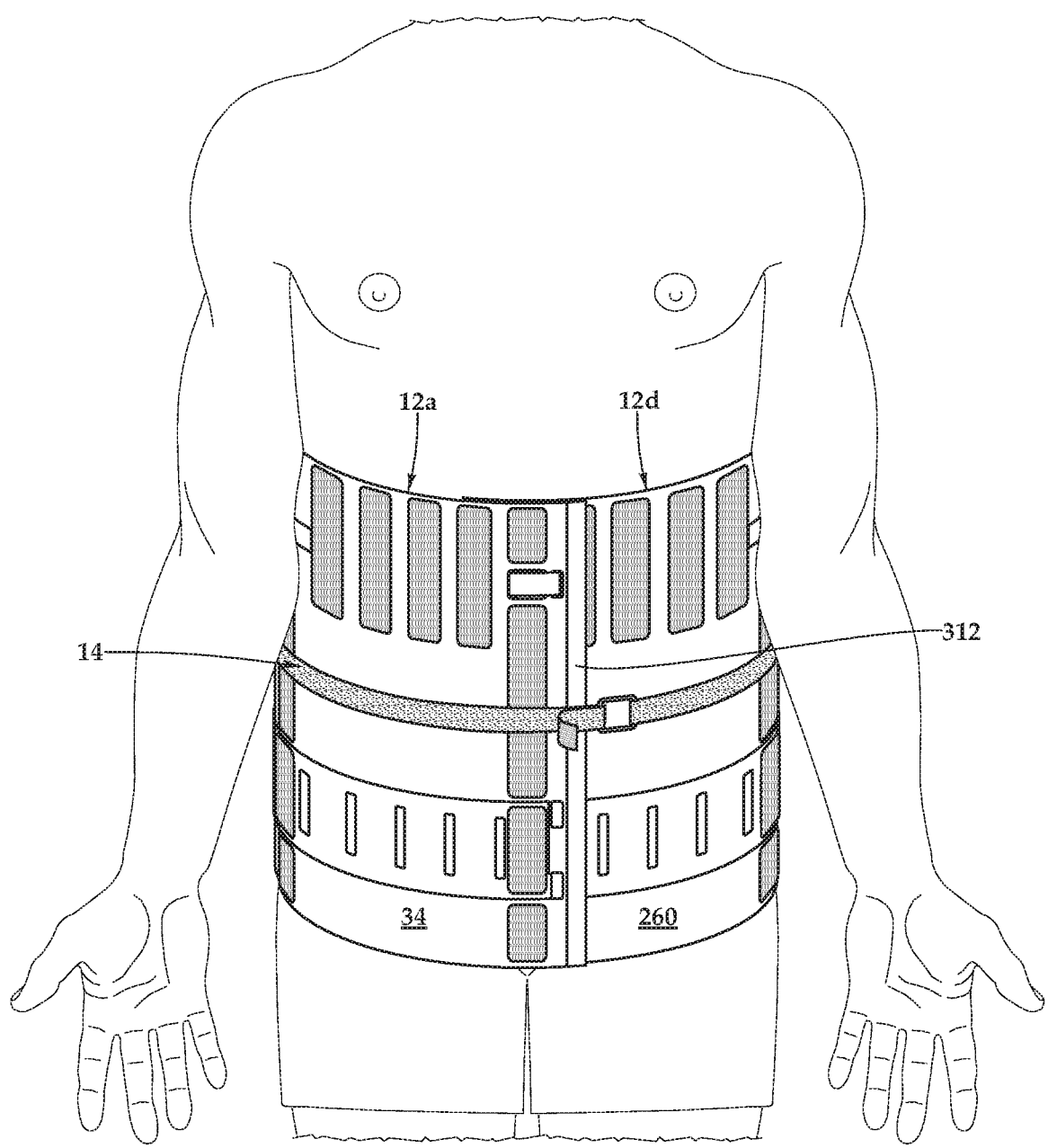
FIG. 12B is a perspective view of the splint system of FIGS. 1 and 12A providing the orthopedic field splint for medical use to address the fractured pelvis.

In FIG. 11A and FIG. 11B, the splint system 10 utilizes the orthopedic field splint 12a, the orthopedic field splint 12b, the orthopedic field splint 12c, the orthopedic field splint 12d, and the orthopedic field splint 12e with end-to-end connections 300a, 300b, 300c and side-to-side connections 310a, 310b to splint a femur E. In FIG. 12A and FIG. 12B, the splint system 10 utilizes the orthopedic field splint 12a, the orthopedic field splint 12b, the orthopedic field splint 12c, and the orthopedic field splint 12d with three side-to-side connections 310a, 310c (only two depicted) and an overlapping connection 312 to splint a pelvis P. In FIG. 9A through FIG. 12B, various combinations of the orthopedic field splints 12 are shown with the straps 14 and the rigid slats 16. It should be appreciated that as appropriate, the sling 18, the traction assembly 20, and the attachment cords 22 are utilized.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An orthopedic field splint system comprising:
   first and second orthopedic field splints, each of the first and second orthopedic field splints including:
   a body having an inner surface and an outer surface, the body having first and second sides, the body having a longitudinal axis from a connector end to a receptacle end, the body having flexion movement parallel to the longitudinal axis from a horizontal axial plane to a rolled sleeve, the body having extension movement parallel to the longitudinal axis from the rolled sleeve to the horizontal axial plane;
   a coupling member hingedly connected to the inner surface of the body proximate the connector end, the coupling member being located in overlapping releasable engagement with the body in a closed retracted position, the coupling member extending beyond the connector end of the body in an open extended position;
   a receiving pocket connected to the outer surface of the body proximate to the receptacle end, the receiving pocket and the coupling member having mutually completing mating forms; and
   a plurality of sleeves extending longitudinally through the body, each of the plurality of sleeves being parallel to the longitudinal axis, each of the plurality of sleeves being configured to accept a rigid slat; and
   the coupling member of the first orthopedic field splint being in the open extended position and inserted into the receiving pocket of the second orthopedic field splint,
   whereby the connector end of the first orthopedic field splint is releasably mated with the receptacle end of the second orthopedic field splint to form a larger, continuous and non-articulated orthopedic field splint with alignment of the plurality of sleeves of the first and second orthopedic field splints for acceptance of the rigid slat therethrough.

2. The orthopedic field splint system as recited in claim 1, wherein each of the first and second orthopedic field splints further comprise a fastener located along the first side and the inner surface of the flexible body.

3. The orthopedic field splint system as recited in claim 2, wherein each fastener has a furled configuration and unfurled configuration.

4. The orthopedic field splint system as recited in claim 2, wherein each fastener further comprises a hook-and-loop fastener.

5. The orthopedic field splint system as recited in claim 1, wherein each of the first and second orthopedic field splints further comprise a fastener located along the second side and the outer surface of the flexible body.

6. The orthopedic field splint system as recited in claim 5, wherein each fastener has a furled configuration and unfurled configuration.

7. The orthopedic field splint system as recited in claim 5, wherein each fastener further comprises a hook-and-loop fastener.

8. The orthopedic field splint system as recited in claim 1, wherein each of the first and second orthopedic field splints further comprise an attachment strap slidably attached to the body, the attachment strap configured for movement parallel to the longitudinal axis.

9. The orthopedic field splint system as recited in claim 1, wherein, with respect to each of the first and second orthopedic field splints, the coupling member is folded against the inner surface of the opposing orthopedic field splint and releasably held thereto by a fastener.

10. The orthopedic field splint system as recited in claim 9, wherein the fastener further comprises a hook-and-loop fastener.

11. The orthopedic field splint system as recited in claim 1, wherein, with respect to each of the first and second orthopedic field splints, the receiving pocket is positioned against the outer surface of the opposing orthopedic field splint and releasably held thereto by a fastener.

12. The orthopedic field splint system as recited in claim 11, wherein the fastener further comprises a hook-and-loop fastener.

13. The orthopedic field splint system as recited in claim 1, wherein, with respect to each of the first and second orthopedic field splints further comprise, the body further comprises a material selected from the group consisting of a nylon fabric, a ballistic nylon fabric, a polyester and cotton blended fabric, and polyester fabric.

14. The orthopedic field splint system as recited in claim 1, wherein, with respect to each of the first and second orthopedic field splints, the body further comprises a rectangular shape.

15. The orthopedic field splint system as recited in claim 1, wherein, with respect to each of the first and second orthopedic field splints, the coupling member further comprises a material selected from the group consisting of a nylon fabric, a ballistic nylon fabric, a polyester and cotton blended fabric, and polyester fabric.

16. The orthopedic field splint system as recited in claim 1, wherein, with respect to each of the first and second orthopedic field splints, the receiving pocket further comprises a material selected from the group consisting of a nylon fabric, a ballistic nylon fabric, a polyester and cotton blended fabric, and polyester fabric.

17. The orthopedic field splint system as recited in claim 1, wherein, with respect to each of the first and second orthopedic field splints, the rigid slat is selected from the group consisting of wood, metal, plastic, and composite.

18. The orthopedic field splint system as recited in claim 1, wherein, with respect to each of the first and second orthopedic field splints, the inner surface is configured to contact a body part of a patient.

19. An orthopedic field splint system comprising:
first and second orthopedic field splints, each of the first and second orthopedic field splints including:
a body having an inner surface and an outer surface, the body having first and second sides, the body having a longitudinal axis from a connector end to a receptacle end, the body having flexion movement parallel to the longitudinal axis from a horizontal axial plane to a rolled sleeve, the body having extension movement parallel to the longitudinal axis from the rolled sleeve to the horizontal axial plane;
a coupling member hingedly connected to the inner surface of the body proximate the connector end, the coupling member being located in overlapping releasable engagement with the body in a closed retracted position, the coupling member extending beyond the connector end of the body in an open extended position;
a receiving pocket connected to the outer surface of the body proximate to the receptacle end, the receiving pocket and the coupling member having mutually completing mating forms; and
a plurality of sleeves extending longitudinally through the body, each of the plurality of sleeves being parallel to the longitudinal axis, each of the plurality of sleeves being configured to accept a rigid slat;
the coupling member of the first orthopedic field splint being in the open extended position and inserted into the receiving pocket of the second orthopedic field splint;
the connector end of the first orthopedic field splint is releasably mated with the receptacle end of the second orthopedic field splint to form a larger, continuous and non-articulated orthopedic field splint with alignment of the plurality of sleeves of the first and second orthopedic field splints for acceptance of the rigid slat therethrough; and
the first orthopedic field splint and the second orthopedic field splint forming a portion of a medical device to address a fracture selected from the group consisting of fractured humerus, fractured tibia, fractured femur, and fractured pelvis.

* * * * *